United States Patent [19]
Goettsche et al.

[11] Patent Number: 5,276,029
[45] Date of Patent: Jan. 4, 1994

[54] WOOD PRESERVATIVE COMPOSITIONS HAVING ACTIVITY AGAINST TERMITES AND FUNGI

[75] Inventors: Reimer Goettsche; Hans-Volker Borck, both of Baden-Baden, Fed. Rep. of Germany

[73] Assignee: Dr. Wolman GmbH, Sinzheim, Fed. Rep. of Germany

[21] Appl. No.: 607,691

[22] Filed: Nov. 1, 1990

[30] Foreign Application Priority Data

Nov. 11, 1989 [DE] Fed. Rep. of Germany ....... 3937658

[51] Int. Cl.$^5$ .................. A61K 31/535; A01N 33/04; A01N 55/02
[52] U.S. Cl. ............... 514/231.2; 514/239.5; 514/499; 514/500; 514/611; 514/645; 514/663; 514/673; 514/674; 424/630; 424/632; 424/633; 424/634; 424/635; 424/637; 424/638
[58] Field of Search ............... 514/499, 500, 663, 673, 514/231.2, 239.5, 611, 645, 674; 424/630, 632, 633, 634, 635, 637, 638

[56] References Cited

U.S. PATENT DOCUMENTS

| | | | |
|---|---|---|---|
| 3,468,885 | 9/1969 | Sanne et al. | 544/178 |
| 4,048,324 | 9/1977 | Kohn | 514/500 |
| 4,143,153 | 3/1979 | Pommer et al. | 514/494 |
| 4,761,179 | 8/1988 | Goettsche et al. | 424/18.32 |
| 4,857,322 | 8/1989 | Goettsche et al. | 424/633 |
| 5,021,459 | 6/1991 | Goettsche | 514/663 |

FOREIGN PATENT DOCUMENTS

| | | | |
|---|---|---|---|
| 0234461 | 9/1987 | European Pat. Off. | B27K 3/50 |
| 2752135 | 5/1978 | Fed. Rep. of Germany | A01N 43/40 |
| 57-50902 | 3/1982 | Japan | 514/663 |
| 8203817 | 11/1982 | World Int. Prop. O. | |

OTHER PUBLICATIONS

Chemical Abstracts 105:56204y (1986); abstracting Chem. et al., "Termite resistance of . . . " For. Prod. J., 1986, 36(5), pp. 18-20.

*Primary Examiner*—Allen J. Robinson
*Assistant Examiner*—John D. Pak
*Attorney, Agent, or Firm*—Oblon, Spivak, McClelland, Maier & Neustadt

[57] ABSTRACT

Wood preservatives contain a copper salt, a polyamine and a fatty amine and are used for preserving wood from fungi and termites.

15 Claims, No Drawings

WOOD PRESERVATIVE COMPOSITIONS HAVING ACTIVITY AGAINST TERMITES AND FUNGI

The present invention relates to a wood preservative having activity against fungi and termites and based on a copper salt, a polyamine and a fatty amine.

Water-soluble wood preservatives based on bis-(N-cyclohexyldiazeniumdioxy)-copper (Cu—HDO), a polyamine and a complex-forming carboxylic acid are known, but they have no activity against termites (EP-A-234 461).

Furthermore, wood preservatives based on a copper compound, an aliphatic carboxylic acid and a polyamine are known (EP-A-270 848); their activity against termites is unsatisfactory.

The fungicidal activity of fatty amines (e.g. dimethylalkylamines), tridemorph (N-tridecyl-2,6-dimethylmorpholine) and fenpropimorph (4-(3-para-tertbutyl-phenyl-2-methylpropyl)-2,6-cis-dimethylmorpholine) is known (U.S. Pat. No. 3,468,885 and DE-27 52 135).

We have found that water-soluble wood preservatives based on copper salts of acids (for example aliphatic, water-insoluble carboxylic acids or bis-(N-cyclohexyldiazeniumdioxy)-copper), a polyamine (e.g. dipropylenetriamine) and a fatty amine (e.g. N,N-dimethyl-N-($C_{12}$–$C_{14}$-alkyl)-amine) and, if required, tridemorph or fenpropimorph and, if necessary, an emulsifier and, if necessary, a complex-forming carboxylic acid surprisingly also have good activity against termites in addition to the activity against fungi.

The copper salts of, for example $C_5$–$C_{20}$-monocarboxylic acids, such as hexanoic acid, heptanoic acid, octanoic acid, nonanoic acid, decanoic acid, 2-ethylheptanoic acid, isooctanoic acid, isononanoic acid, isodecanoic acid, VERSATIC acids and neocarboxylic acids (highly branched monocarboxyliclvids) or polycarboxylic acids, such as $C_5$–$C_{20}$-dicarboxylic acids, e.g. azelaic acid, sebacic acid or decanedicarboxylic acid, can be used.

Instead of the copper salt, it is also possible to use mixtures of the abovementioned acids or of the corresponding water-soluble alkali metal or amine salts with water-soluble or water-insoluble copper compounds, e.g. copper acetate, copper sulfate, copper fluoborate, copper hydroxide, copper oxide, basic copper carbonate, copper borate, copper fluoride or copper fluorophosphate.

Some of the copper may be replaced by corresponding zinc compounds.

The same applies to CU—HDO, where, for example, mixtures of N-cyclohexyldiazeniumdioxy-Potassium (K—HDO) with the abovementioned copper compounds can be used.

Examples of particularly suitable polyamines are aliphatic polyamines, alkylenepolyamines of 3 to 9 carbon atoms and 2 to 4 nitrogen atoms, e.g. 1,3-diaminopropane, 1-methylamino-3-aminopropane, dipropylenetriamine, tripropylenetetramine, ethylenediamine, diethylenetriamine, triethylenetetramine and aminoethylethanolamine.

The fatty amines are of, for example, the general formulae

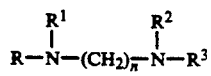

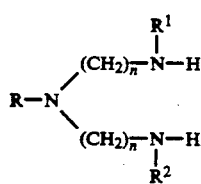

n = 1-20 where R is $C_6$–$C_{20}$-alkyl and/or $C_6$–$C_{20}$-hydroxyalkyl and $R^1$, $R^2$ and $R^3$ independently of one another are each hydrogen or lower alkyl ($C_1$–$C_4$-alkyl) or have the same meanings as R or are each $C_1$–$C_4$-alkyl-substituted or halogen-substituted benzyl.

The fatty amines can be used as individual substances or as mixtures.

The fatty amines or tridemorph or fenpropimorph can be used in particular in the form of salts of water-soluble and/or water-insoluble carboxylic acids and/or dicarboxylic acids, for example salts of acetic acid, propionic acid, in particular 2-ethylhexanoic acid, isooctanoic acid, isononanoic acid or sebacic acid. The acid may be added in excess, depending on the pH to be established for the concentrate and the aqueous impregnating solution.

The salts can be used as individual substances or as mixtures, for example also as mixtures with fatty amines.

Examples of suitable fatty amines are dimethyl-$C_{10}$–$C_{18}$-alkylamines, methyldioctylamine, methyldidecylamine, tridecylamine, octyldiethanolamine, N,N'-didodecyl-1,3-propylenediamine, $C_{13}$–$C_{15}$-alkyl-trimethylenediaminelaurylpropylenediamine and N,N-bis-(3-aminoprop-yl)-laurylamine.

The fatty amines or tridemorph or fenpropimorph are incorporated in the formulations (concentrates) or their aqueous impregnating solutions if necessary with the additional use of emulsifiers.

Ionic and/or nonionic emulsifiers are suitable here, for example ethoxylated nonylphenols, ethoxylated monoalkylamines, quaternary ammonium compounds and/or phosphonium compounds.

A quaternary ammonium compound is, for example, a compound of the general formula $R^1R^2R^3R^4N^+Z^-$, where $R^1$ is alkyl of 8 to 20 carbon atoms, in particular alkyl of 12 to 20 carbon atoms, or benzyl which is unsubstituted or substituted by $C_1$–$C_{20}$-alkyl or halogen, $R^2$ is $C_1$–$C_6$-alkyl, $C_3$–$C_9$-alkoxyalkyl, EO or PO where n is 1-50, $R^3$ is $C_1$–$C_6$-alkyl, $C_3$- or $C_4$-alkoxy, EO or PO where n is 2-50 and $R^4$ is $C_1$–$C_{20}$-alkyl, or two of the radicals $R^1$ to $R^4$ together with the nitrogen atom form a heterocyclic radical which contains 4 or 5 carbon atoms, 1 or 2 nitrogen atoms and one, two or three double bonds, the carbon atoms being unsubstituted or substituted by $C_1$–$C_4$-alkyl or halogen, and Z is in general an acid radical, for example a radical of an inorganic acid (hydrochloric acid, sulfuric acid or phosphoric acid) or a radical of an organic carboxylic acid (acetic acid or propionic acid).

Particularly suitable effective phosphonium compounds are compounds of the formula $$R_3^1R^2P^+Y^-$$

where $R^1$ is alkyl of 1 to 6 carbon atoms, hydroxyalkyl of 1 to 6 carbon atoms or phenyl, $R^2$ is alkyl of 8 to 18 carbon atoms and Y is an acid radical, in particular a halide anion.

$R^1$ and $R^2$ are preferably straight-chain.

The quaternary phosphonium compounds may be present in the novel concentrates individually or as mixtures. Examples of such phosphonium compounds are trimethyl-n-dodecylphosphonium chloride, triethyl-n-decylphosphonium bromide, tri-n-propyl-n-tetradecylphosphonium chloride, trimethylol-n-hexdecylphosphonium chloride, tri-n-butyl-n-tetradecylphosphonium chloride, tri-n-butyl-n-dodecylphosphonium bromide, tri-n-butyl-n-decylphosphonium chloride, tri-n-butyl-n-hexadecylphosphonium bromide, tri-n-hexyl-n-decylphosphonium chloride, triphenyl-n-dodecylphosphonium chloride, triphenyl-n-tetradecylphosphonium bromide and triphenyl-n-octadecylphosphonium chloride.

When CU—HDO, K—HDO and copper compounds are used, better penetration can advantageously be achieved by additionally using a complex-forming carboxylic acid, e.g. nitrilotriacetic acid, lactic acid or tartaric acid.

The wood preservatives may contain further compounds, for example a compound having a fungicidal anion, e.g. a boron compound, such as an alkali metal borate, an amine borate or boric acid, a fluoride, e.g. potassium fluoride and/or salts of fluoboric acid and/or fluorophosphoric acid and/or difluorophosphoric acid.

The novel concentrates generally contain from 1 to 15% by weight of copper, and the aqueous impregnating solutions contain from 0.01 to 2.0% of copper, depending on the extent to which the wood to be impregnated is threatened.

Suitable concentrates contain, for example,
2.5–50% of a copper salt of an acid,
5.0–50% of a polyamine,
2.5–50% of a fatty amine or its salts,
0–35% of tridemorph, fenpropimorph or their salts,
0–30% of a fungicidal, diffusing anion,
0–50% of an emulsifier and
0–25% of a complex-forming carboxylic acid,
the sum of the percentages by weight being 100%.

The weight ratio of CU—HDO and/or the copper salt of a water-insoluble mono- or polycarboxylic acid to the fatty amine, tridemorph or fenpropimorph is, for example, from 5 : 1 to 1 : 5.

If necessary, minor amounts of other components, such as other amines, ammonia, corrosion inhibitors and, if required, water and/or polar water-miscible solvents may be present, but the amounts of these can generally be kept small and they are essentially present for handling purposes.

The present invention relates both to the concentrates and to the impregnating solutions which can be prepared from them by dilution with water.

The pH of the impregnation solution is in general from 6 to 11, particularly frequently from 7.5 to 9.5.

In the preparation of the wood preservatives, with or without the addition of water, highly concentrated pastes or liquid concentrates are formed.

To extend the action spectrum, additional fungicides, for example organotin compounds, such as tributyltin compounds (TBT), eg. tributyltin oxide (TBTO), TBT-HDO, TBT versatoate, TBT naphthenate or TBT benzoate, may be incorporated.

The impregnating solutions can be used for preserving wood on the one hand by manual methods, for example spraying, brushing on, immersion or trough impregnation, or by large-scale industrial processes, such as the pressure process or vacuum process. Wood is understood as meaning solid wood and woodworking materials, for example particle boards and plywood. In the case of the woodworking materials, it is advisable to carry out the impregnation by the glue mixing method. The wood preservatives have a fungicidal action corresponding to the action of known wood preservatives.

The Examples which follow illustrate the invention.

The activity against termites was demonstrated with the aggressive termite species Heterotermes indicola, which has more aggressive behavior than the termite species usually used for testing.

5 test blocks (15×25×50 mm) of pine sapwood were impregnated and were washed thoroughly with water several times after a fixing time of 4 weeks, and 1 test block was placed in a test vessel after a further 7 days for the termite test. 200 animals were counted for the test and were placed in the test vessel. The activity of the termites was checked visually at intervals of 7 days. When activity was no longer observed, the blocks were removed from the test vessel and evaluated, and the number of surviving termites was determined. Where the animals still exhibited activity, the blocks remained in the test vessel for a maximum of 6 weeks, after which the attack by the termites was evaluated visually.

COMPARATIVE EXAMPLE A (not according to the invention) (% by weight)

25.0% of CU—HDO,
22.5% of diethylenetriamine,
12.5% of nitrilotriacetic acid and
40.0% of water.

The concentrate was diluted with water, i.e. 2 parts by weight of concentrate and 98 parts by weight of water (application concentration 2%) or 4 parts by weight of concentrate and 96 parts by weight of water (application concentration 4%).

Results of termite test
2% application concentration = 14.8 kg of concentrate/m$^3$
Test time : 6 weeks
Attack : Block severely eaten away
Surviving animals : more than 150
4% application concentration = 19.1 kg of concentrate /m$^3$
Test time : 6 weeks
Attack : Block severely eaten away
Surviving animals : more than 150

COMPARATIVE EXAMPLE B (not according to the invention)

13.5% of K—HDO,
6.25% of nitrilotriacetic acid,
10.00% of diethylenetriamine,
6.25% of boric acid,
4.00% of Cu(OH)$_2$CuCO$_3$ and
60.0% of water
= 12.5% of CU—HDO
4% application concentration = 28.4 kg of concentrate/m$^3$
Test time : 6 weeks Attack : Block severely eaten away
Surviving animals : more than 150

COMPARATIVE EXAMPLE C (not according to the invention)

13.3% of basic copper carbonate,
28% of dipropylenetriamine,
10.0% of boric acid,
36.7% of isooctanoic acid and
12.0% of water
4% application concentration=28.9 kg of concentrate/m$^3$
Test time : 6 weeks
Attack : Block gnawed
Surviving animals : more than 50

COMPARATIVE EXAMPLE D (not according to the invention)

10.0% of copper carbonate,
16.5% of 1,3-diaminopropane,
27.5% of 2-ethylhexanoic acid,
4.0% of boric acid,
2.5% of nitrilotriacetic acid,
5.0% of K—HDO and
34.5% of water
4% application concentration=28.7 kg of concentrate/m$^3$
Test time : 6 weeks
Attack : Block gnawed or eaten away
Surviving animals : more than 50

COMPARATIVE EXAMPLE E (not according to the invention)

30% of dimethyl-C$_{12}$–C$_{14}$-alkylamine,
12% of tridemorph,
20% of 2-ethylhexanoic acid,
30% of ethoxylated coconut fatty amine (density 0.96 g/cm$^3$ at 50° C.)
2% application concentration=14.5 kg of concentrate/m$^3$
Test time : 6 weeks
Attack : Block gnawed or eaten away
Surviving animals : more than 50

COMPARATIVE EXAMPLE F (not according to the invention)

50% of dimethyl-C$_{12}$–C$_{14}$-alkylamine,
4% of acetic acid,
12% of sebacic acid,
30% of ethoxylated coconut fatty amine and
4% of water
2% application concentration=14.6 kg of concentrate/m$^3$
Test time : 6 weeks
Attack : Block gnawed or eaten away
Surviving animals : more than 100

Examples according to the invention

EXAMPLE 1

10.1% of K—HDO,
8.2% of diethylenetriamine,
3.0% of Cu(OH)$_2$CuCO$_3$,
4.7% of nitrilotriacetic acid,
4.7% of boric acid,
7.5% of dimethyl-C$_{12}$–C$_{14}$-alkylamine,
5.0% of ethoxylated coconut fatty amine and
39.6% of water
(=9.4% of CU—HDO)
4% application concentration=28.3 kg of concentrate/m$^3$
Test time : 2 weeks
Attack : No attack
Surviving animals : 0

EXAMPLE 2

6.75% of K—HDO,
5.50% of diethylenetriamine,
3.10% of nitrilotriacetic acid,
2.00% of Cu(OH)$_2$CuCO$_3$,
25.00% of dimethyl-C$_{12}$–C$_{14}$-alkylamine,
2.00% of acetic acid,
6.00% of sebacic acid,
15.00% of ethoxylated coconut fatty amine and
34.65% of water
(=6.25% of CU—HDO)
4% application concentration=28.60 kg of concentrate/m$^3$
Test time : 2 weeks
Attack : No attack
Surviving animals : 0

EXAMPLE 3

7.50% of Cu(OH)$_2$CuCO$_3$
18.75% of isooctanoic acid,
4.80% of K—HDO,
1.90% of tactic acid,
3.00% of boric acid,
9.75% of 1,3-diaminopropane,
7.50% of dimethyl-C$_{12}$–C$_{14}$-alkylamine
5.00% of tridemorph,
2.50% of 2-ethylhexanoic acid,
7.50% of ethoxylated coconut fatty amine and
31.80% of water
4% application concentration=28.7 kg of concentrate/m$^3$
Test time : 4 weeks
Attack : A slight trace of gnawing
Surviving animals 0

EXAMPLE 4

5.0% of Cu(OH)$_2$CuCO$_3$,
12.5% of isooctanoic acid,
3.2% of K—HDO,
1.3% of tactic acid,
2.0% of boric acid,
6.5% of 1,3-diaminopropane,
15.0% of dimethyl-C$_{12}$–C$_{14}$-alkylamine,
10.0% of tridemorph,
5.0% of 2-ethylhexanoic acid,
5.0% of sebacic acid,
10.0% of ethoxylated coconut fatty amine and
24.5% of water
4% application concentration=28.9 kg of concentrate/m$^3$
Test time : 2 weeks
Attack : No attack
Surviving animals : 0

EXAMPLE 5

6.70% of Cu(OH)$_2$CuCO$_3$,
16.70% of 2-ethylhexanoic acid,
4.30% of K-HDO,
2.70% of boric acid,
1.70% of tactic acid, 4.50% of 1,3-diaminopropane,
5.00% of dipropylenetriamine,
10.00% of dimethyl-$C_{12}$-$C_{14}$-alkylamine,
6.67% of methyl-$C_8$-$C_{10}$-dialkylamine,
3.33% of isooctanoic acid,
3.33% of sebacic acid,
10.0% of ethoxylated coconut fatty amine and
25.07% of water
3% application concentration=21.5 kg of concentrate/m$^3$
Test time : 2 weeks
Attack : No attack
Surviving animals : 0

EXAMPLE 6

4.5% of Cu(OH)$_2$,
12.5% of 2-ethylhexanoic acid,
3.2% of K—HDO,
1.3% of tactic acid,
2.0% of boric acid,
8.0% of dipropylenetriamine,
15.0% of dimethyl-$C_{12}$-$C_{14}$-alkylamine,
10.0% of fenpropimorph,
5.0% of sebacic acid,
15.0% of ethoxylated coconut fatty amine and
23.5% of water
4% application concentration=28.7 kg of concentrate/m$^3$
Test time : 2 weeks
Attack : No attack
Surviving animals : 0

EXAMPLE 7

6.0% of Cu(OH)$_2$,
16.7% of isooctanoic acid,
4.3% of K—HDO,
2.7% of boric acid,
10.0% of dipropylenetriamine,
5.0% of laurylpropylenediamine,
10.0% of dimethyl-$C_{12}$-$C_{14}$-alkylamine,
6.7% of tridemorph,
6.7% of 2-ethylhexanoic acid,
5.0% of ethoxylated coconut fatty amine and
26.9% of water
3% application concentration=21.9 kg of concentrate/m$^3$
Test time : 2 weeks
Attack : No attack
Surviving animals : 0

EXAMPLE 8

6.75% of Cu(OH)$_2$,
18.75% of isooctanoic acid,
4.80% of boric acid,
11.75% of dipropylenetriamine,
7.50% of dimethyl-$C_{12}$-$C_{14}$-alkylamine,
6.50% of N,N-bis-(3-aminopropyl)-laurylamine,
7.50% of 2-ethylhexanoic acid and
34.45%-of water
4% application concentration=28.1 kg of concentrate/m$^3$
Test time : 2 weeks
Attack : No attack
Surviving animals : 0

EXAMPLE 9

7.5% of CuO,
28.0% of 2-ethylhexanoic acid,
13.0% of dipropylenetriamine,
5.0% of tridemorph,
7.5% of dimethyl-$C_{12}$-$C_{14}$-alkylamine,
2.3% of lactic acid,
12.5% of ethoxylated nonylphenol, degree of ethoxylation
about 10, and
24.2% of water
4% application concentration=28.3 kg of concentrate/m$^3$
Test time : 4 weeks
Attack : 1 slight trace of gnawing
Surviving animals : 0

EXAMPLE 10

7.5% of CuO,
28.0% of isooctanoic acid,
13.0% of dipropylenetriamine,
5.0% of tridemorph,
7.5% of dimethyl-$C_{12}$-$C_{14}$-alkylamine,
2.3% of lactic acid,
12.5% of ethoxylated nonylphenol, degree of ethoxylation
about 10, and
24.2% of water
4% application concentration=28.6 kg of concentrate/m$^3$
Test time : 3 weeks
Attack : No attack
Surviving animals : 0

We claim:
1. A wood preservative composition, comprising:
(A) from 5.0 to 50% by weight of a polyamine having from 3 to 9 carbon atoms and from 2 to 4 nitrogen atoms;
(B) from 2.5 to 50% by weight of a fatty amine of the formula NRR$^1$R$^2$, wherein R is $C_6$-$C_{20}$-alkyl and R$^1$ and R$^2$ are each independently hydrogen or $C_1$-$C_4$-alkyl, or $C_6$-$C_{20}$-alkyl; and
(C) bis(N-cyclohexyldiazeniumdioxy)copper in a weight ratio of from 5:1 to 1:5 with respect to said fatty amine.
2. The composition of claim 11, further comprising from 2.5 to 50% by weight of a copper salt of an acid selected from the group consisting of $C_5$-$C_{20}$-monocarboxylic acids and $C_5$-$C_{20}$-dicarboxylic acids.
3. The composition of claim 1, where said polyamine is dipropylenetriamine.
4. The composition of claim 1, where said polyamine is diethylenetriamine.
5. The composition of claim 1, where said polyamine is 1,3-diaminopropane.
6. The composition of claim 1, where said fatty amine is N,N-dimethyl-N-($_{12}$-$C_{14}$-alkyl)amine.
7. The composition of claim 2, wherein said $C_5$-$C_{20}$-monocarboxylic acid is selected from the group consisting of hexanoic acid, heptanoic acid, octanoic acid, nonanoic acid, decanoic acid, undecanoic acid and isomers thereof, and said $C_5$-$C_{20}$-dicarboxylic acid is selected from the group consisting of azelaic acid, sebacic acid and decanedicarboxylic acid.
8. The composition of claim 2, wherein said acid is a $C_5$-$C_{20}$-monocarboxylic acid selected from the group consisting of hexanoic acid, heptanoic acid, octanoic acid, nonanoic acid, decanoic acid, 2-ethylhexanoic acid, 2-ethylheptanoic acid, isooctanoic acid, isononanoic acid and isodecanoic acid.

9. The composition of claim 2, wherein said acid is a $C_5$–$C_{20}$-dicarboxylic acid selected from the group consisting of azeleic acid, sebacic acid and decanedicarboxylic acid.

10. The composition of claim 1, further comprising N-tridecyl-2,6-dimethylmorpholine or 4-(3-para-tert-butylphenyl-2-methylpropylene)-2,6-cis-dimethylmorpholine.

11. The composition of claim 2, further comprising N-tridecyl-2,6-dimethylmorpholine or 4-(3-para-tert-butylphenyl-2-methylpropylene)-2,6-cis-dimethylmorpholine.

12. The composition of claim 1, wherein said fatty amine is selected from the group consisting of dimethyl-($C_{10}$–$C_{18}$-alkyl)amines, methyldioctylamine, methyldidecylamine, tridecylamine, N,N'-didodecyl-1,3-propylene diamine, $C_{13}$–$C_{15}$-alkyltrimethylenediaminelaurylpropylenediamine and N,N-bis-(3-aminopropyl)-laurylamine.

13. An impregnating solution for preserving wood from fungi and termites, prepared by diluting a wood preservative as claimed in claim 1 with water.

14. A process for preserving wood from fungi and termites, wherein the wood is treated with an effective wood preserving amount of a wood preservative as claimed in claim 1.

15. A process for preserving wood from fungi and termites, wherein the wood is impregnated with an effective wood preserving amount of an aqueous impregnating solution which has been prepared by diluting a wood preservative as claimed in claim 1 with water.

* * * * *